(12) United States Patent
Hashimoto et al.

(10) Patent No.: US 8,084,214 B2
(45) Date of Patent: Dec. 27, 2011

(54) TREATMENT SOLUTION, METHOD FOR PRETREATMENT, METHOD FOR ACQUIRING INFORMATION AND METHOD FOR DETECTION

(75) Inventors: Hiroyuki Hashimoto, Yokohama (JP); Manabu Komatsu, Kawasaki (JP); Satoru Hatakeyama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 53 days.

(21) Appl. No.: 12/098,822

(22) Filed: Apr. 7, 2008

(65) Prior Publication Data
US 2008/0268497 A1 Oct. 30, 2008

(30) Foreign Application Priority Data
Apr. 27, 2007 (JP) .................................. 2007-118899

(51) Int. Cl.
G01N 33/53 (2006.01)
(52) U.S. Cl. .............................. 435/7.1; 435/7.2; 436/85
(58) Field of Classification Search ........................ None
See application file for complete search history.

(56) References Cited

U.S. PATENT DOCUMENTS

| | | | |
|---|---|---|---|
| 6,395,652 B2* | 5/2002 | Kim et al. ...................... | 438/792 |
| 7,188,031 B1 | 3/2007 | Okamoto et al. | |
| 2004/0132080 A1 | 7/2004 | Kawaguchi et al. | |
| 2005/0054648 A1* | 3/2005 | Mitchell et al. ................ | 514/249 |
| 2006/0183235 A1* | 8/2006 | Hashimoto et al. ............. | 436/86 |
| 2006/0275811 A1 | 12/2006 | Hatakeyama et al. | |
| 2007/0105087 A1 | 5/2007 | Ban et al. | |
| 2008/0090267 A1 | 4/2008 | Komatsu et al. | |
| 2008/0187461 A1 | 8/2008 | Hatakeyama et al. | |

FOREIGN PATENT DOCUMENTS

| | | |
|---|---|---|
| JP | 8273530 | 10/1996 |
| JP | 3207706 | 7/2001 |
| JP | 2004085546 | 3/2004 |
| JP | 3658397 | 3/2005 |
| JP | 2006010658 | 1/2006 |
| WO | 2005/003715 | 1/2005 |

OTHER PUBLICATIONS

Huang et al. (Langmuir et al. 2003, vol. 19, p. 7498-7502).*
Kim et al. (Analytical Chem 2006 vol. 78, p. 1913-1920.*
A. Marcus and N. Winograd, "Metal Nanoparticle Deposition for TOF-SIMS Signal Enhancement of Polymers", Anal. Chemistry, 78, pp. 141-148 (2006).
S.G. Ostrowski, et al., "Single-Cell Level Mass Spectrometric Imaging", Encyclopedia of Nanoscience and Nanotechnology, pp. 1-11 (2006).
Y.P. Kim, et al., "Gold Nanoparticle-Enhanced Secondary Ion Mass Spectrometry Imaging of Peptides on Self-Assembled Monolayers", Anal. Chemistry, 78, pp. 1913-1920 (2006).
H. Hashimoto, et al., "Quantitative TOF-SIMS imaging of DNA microarrays produced by bubble jet printing technique and the role of TOF-SIMS in life science industry", Applied Surface Science, 231-232 (2004) pp. 385-391.
U.S. Appl. No. 11/913,045, International filing date May 30, 2006, Shiotsuka, et al.
U.S. Appl. No. 12/113,795, filed May 1, 2008, Murayama, et al.
U.S. Appl. No. 11/913,047, International filing date May 29, 2006, Shiotsuka, et al.
U.S. Appl. No. 12/117,527, filed May, 8, 2008, Komatsu, et al.
U.S. Appl. No. 11/645,028, filed Dec. 26, 2008, Hatakeyama.
U.S. Appl. No. 12/120,512, filed May 14, 2008, Komatsu, et al.
Isobe, et al., Eds., "Experimental Medicine Separate Volume, Experimental Course of Post-Genome Age 2, Proteome Analysis Method" (2000).
Gole, et al., Pepsin-Gold Colloid Conjugates: Preparation, Characterization, and Enzymatic Activity, Langmuir, 2001, vol. 17, pp. 1675-1679.
European Search Report dated Aug. 12, 2008 in European Application No. 08007520.3.
Dykman, et al., "A protein assay based on colloidal gold conjugates with trypsin", Analytical Biochemistry, vol. 341, 2005, pp. 16-21.
Altelaar, et al., "Gold-Enhanced Biomolecular Surface Imaging of Cells and Tissue by SIMS and MALDI Mass Spectrometry", Analytical Chemistry, vol. 78, 2006, pp. 734-742.
Heeren, et al., "Why don't biologists use SIMS? A critical evaluation of imaging MS", Applied Surface Science, vol. 252, 2006, pp. 6827-6835.
Groseclose, et al., "Identification of proteins directly from tissue: in situ tryptic digestions coupled with imaging mass spectrometry", Journal of Mass Spectrometry, vol. 42, 2007, pp. 254-262.
Shimma, et al., "A Novel Approach to in situ Proteome Analysis Using Chemical Inkjet Printing Technology and MALDI-QIT-TOF Tandem Mass Spectrometer", J. Mass Spectrom, Soc. Jpn, vol. 54, No. 4, 2006, pp. 133-140.
Yee, et al., "Recombinant Trypsin Production in High Cell Density Fed-Batch Cultures in *Escherichia coli*", Biotechnology and Bioengineering, vol. 41, 1993, pp. 781-790.

* cited by examiner

*Primary Examiner* — Jacob Cheu
(74) *Attorney, Agent, or Firm* — Fitzpatrick, Cella, Harper & Scinto (57) ABSTRACT

The present invention intends to provide a high sensitivity method for identifying the type of a protein contained in each cell with a diameter of ten to several tens μm and a sample treatment solution required for it. The above is achieved by three steps of (1) treating a slice of a diseased tissue with an aqueous solution containing gold particles and a digestive enzyme, and digesting restrictively a protein of interest, (2) measuring a 2-dimensional distribution of fragmented peptides by TOF-SIMS, and (3) visualizing a 2-dimensional distribution of the target protein in the slice of the diseased tissue using the results of the proteome analysis and by means of a numerical analysis.

3 Claims, 3 Drawing Sheets

```
              10         20         30         40         50         60
     atgcatcccctgcttatccttgcctttgtgggagctgctgtggctttcccctcggacgac
      M  H  P  L  L  I  L  A  F  V  G  A  A  V  A  F  P  S  D  D 70         80         90        100        110        120
     gatgacaagatcgtcgggggctacacctgcgcagagaattccgtcccttaccaggtgtcc
      D  D  K  I  V  G  G  Y  T  C  A  E  N  S  V  P  Y  Q  V  S 130        140        150        160        170        180
     ctgaatgctggctaccacttctgcgggggctccctcatcaatgaccagtgggtggtgtcc
      L  N  A  G  Y  H  F  C  G  G  S  L  I  N  D  Q  W  V  V  S 190        200        210        220        230        240
     gcggctcactgctaccagtaccacatccaggtgaggctgggagaatacaacattgatgtc
      A  A  H  C  Y  Q  Y  H  I  Q  V  R  L  G  E  Y  N  I  D  V 250        260        270        280        290        300
     ttggagggtggtgagcagttcatcgatgcgtccaagatcatccgccacccaagtacagc
      L  E  G  G  E  Q  F  I  D  A  S  K  I  I  R  H  P  K  Y  S 310        320        330        340        350        360
     agctggactctggacaatgacatcctgctgatcaaactctccacgcctgcggtcatcaat
      S  W  T  L  D  N  D  I  L  L  I  K  L  S  T  P  A  V  I  N 370        380        390        400        410        420
     gcccgggtgtccaccttgctgctgcccagtgcctgtgcttccgcaggcacagagtgcctc
      A  R  V  S  T  L  L  L  P  S  A  C  A  S  A  G  T  E  C  L 430        440        450        460        470        480
     atctccggctggggcaacacccctgagcagtggcgtcaactacccggacctgctgcaatgc
      I  S  G  W  G  N  T  L  S  S  G  V  N  Y  P  D  L  L  Q  C 490        500        510        520        530        540
     ctggtggccccgctgctgagccacgccgactgtgaagcctcataccctggacagatcact
      L  V  A  P  L  L  S  H  A  D  C  E  A  S  Y  P  G  Q  I  T

550        560        570        580        590        600
     aacaacatgatctgcgctggcttcctggaaggaggcaaggattcctgccagggtgactct
      N  N  M  I  C  A  G  F  L  E  G  G  K  D  S  C  Q  G  D  S 610        620        630        640        650        660
     ggcggccctgtggcttgcaacggacagctccagggcattgtgtcctggggctacggctgt
      G  G  P  V  A  C  N  G  Q  L  Q  G  I  V  S  W  G  Y  G  C

670        680        690        700        710        720
     gcccagaagggcaagcctggggtctacaccaaggtctgcaactacgtggactggattcag
      A  Q  K  G  K  P  G  V  Y  T  K  V  C  N  Y  V  D  W  I  Q 730        740        750        760        770
     gagaccatcgccgccaacagcGCTAGCCACCATCATCACCACCATTGC
      E  T  I  A  A  N  S  A  S  H  H  H  H  H  H  C
```

TREATMENT SOLUTION, METHOD FOR PRETREATMENT, METHOD FOR ACQUIRING INFORMATION AND METHOD FOR DETECTION

BACKGROUND OF THE INVENTION

1. Field of the Invention

The present invention relates to a treatment solution used for a pretreatment for analyzing an object in a sample, a method for the pretreatment, a method for acquiring information on the object in the sample, and a method for detecting the presence of a specific object. Especially the present invention relates to a treatment solution used for a pretreatment for analyzing a protein contained in a tissue or a cell, a method for the pretreatment, a method for acquiring information on the protein contained in a tissue or a cell, and a method for detecting the presence of the protein.

2. Description of the Related Art

The recent progress in genome analysis has been rapidly highlighting the importance of analyses of proteins in the living body as gene products.

The importance of analyzing expression and function of a protein has been long recognized, and development of analysis methods therefor has been continued. Fundamentally, they are based on the combination of the techniques of:
(1) separation and purification by two-dimensional electrophoresis or high performance liquid chromatography (HPLC), and
(2) a detection system, such as a radioactivation analysis, an optical analysis, a mass spectrometry.

The basic protein analysis technology is called proteome analysis, which is aimed at analyzing a protein produced by a gene and functioning actually in vivo, and discovering a cell function or the cause of a disease. An example of a typical analysis technique includes:
(1) extraction of a protein from a tissue or cell of interest,
(2) separation of the protein by a two-dimensional electrophoresis,
(3) analysis of the protein or its fragments by a mass spectrometry, such as a matrix-assisted laser desorption ionization time-of-flight mass spectrometry (an MALDI-TOFMS), and
(4) identification of the protein using a database, as from a genome project.

An additional example includes:
(1) extraction of a protein from a tissue or cell of interest,
(2) digestion (or denaturation) of the extracted protein,
(3) analysis of the digested (or denatured) protein by a combined system of a liquid chromatography (LC) and an Ion-trap mass spectrometry (Ion-trap MS), and
(4) creation of a database and identification of the protein. ("Experimental Medicine, Separate Volume, Proteome Analysis", edited by Toshiaki Isobe and Nobuhiro Takahashi, Yodosha Co., Ltd., 2000)

For example concerning cancer, such a positive result is being obtained, that a protein related to recurrence or metastasis is becoming uncovered owing to a proteome analysis.

The present inventors proposed a method and an apparatus for acquiring information based on a time of flight secondary ion mass spectrometry (hereinafter abbreviated as "TOF-SIMS") aiming at visualization of a two-dimensional distribution of a protein on a protein chip or a tissue slice (Japanese Patent No. 3658397). By this method, an ionization promoting substance and/or a digestive enzyme is applied by an ink-jet technique to the protein chip or the tissue slice, and information on an identity of the protein (including information on peptides restrictively proteolyzed by the digestive enzyme) is to be visualized by TOF-SIMS maintaining the positional information.

The present inventors have proposed certain developments of the method and apparatus. Namely, an improvement concerning pH of an aqueous solution used by an ink-jet technique, an improvement concerning detection of an intracellular metabolite, and an improvement concerning identification ability for a protein by a combined use of separation and purification techniques, such as electrophoresis or thin-layer chromatography.

To improve the detection sensitivity of TOF-SIMS, a method of using metal particles has been proposed. For example, A. Marcus and N. Winograd reported that the detection sensitivity was improved by depositing nano-particles of gold or silver on the sample surface forming a sub-monolayer (A. Marcus and N. Winograd, Anal. Chem., 78, 141-148 (2006)). Further, Y. P. Kim et al. reported that the ionization efficiency (by TOF-SIMS) of a peptide molecule located on a nano-particle of gold was enhanced by the effect of the gold nano-particle (Y. P. Kim et al., Anal. Chem., 78, 1913-1920 (2006)).

Examples of an SIMS analysis aiming at a single cell include a report by S. G. Ostrowski et al. (S. G. Ostrowski et al., "Single-Cell Level Mass Spectrometric Imaging", Dekker Encyclopedia of Nanoscience and Nanotechnology, pages 1-11 (2006)).

Further, Japanese Patent No. 3207706 discloses a method, by which an aqueous solution containing a metal colloid is applied in a form of droplets to a substrate by an ink-jet method.

SUMMARY OF THE INVENTION

The conventional proteome analysis has been, however, so far directed to a specific tissue, body fluid and blood, and not directly to a cell with a diameter of ten to several tens µm. If a protein in a specific diseased cell, such as a cancer cell, or a protein in a cell adjacent to the cancer cell, or both of them, could be identified, it would contribute to development of a diagnosis device and a drug development-assisting device (for drug candidate screening). It also could in principle determine directly the existence or nonexistence of a protein related to metastasis or recurrence in a possible early cancer cell or a cancer tissue, which would establish a new method for prognostication.

According to the method for acquiring information disclosed by the present inventors, information on a protein on the cell level (including information on peptides restrictively proteolyzed by the digestive enzyme) could be obtained, but it had a drawback that the detection sensitivity was not high enough in some cases.

Although the method of S. G. Ostrowski et al. enabled cell-level imaging based on the mass information by realizing high spatial resolution of SIMS, there was a restriction that the upper limit of the mass/charge ratio (m/z) was about 500. In other words, the method was not adequate to detect "a characteristic fragment ion having the m/z ratio of about 500 to 5000" required to identify from digested fragments a protein before digestion as described in the Japanese Patent No. 3207706 proposed by the present inventors.

The methods of A. Marcus and N. Winograd, or Y. P. Kim et al. disclosed that the co-existence of gold nano-particles (coated or placed under an analyte molecule) improved the detection sensitivity of TOF-SIMS. However, the methods were not directed to digested peptides, and could be difficult for applying to an analysis of a specific protein in a tissue or a cell (a method for uniform digestion was not disclosed).

Further, although the Japanese Patent No. 3207706 disclosed a method, by which an aqueous solution containing a metal colloid was applied in a form of droplets to a substrate by an ink-jet technique, the method was directed to form a conduction line of an electronic device, and no reference was made to an application of a digestive enzyme. Namely, the method can be difficult for applying as it is to a pretreatment for an analysis of a specific protein in a tissue or a cell.

A treatment solution according to the present invention is a treatment solution for a pretreatment for an analysis of an object in a sample, and the treatment solution contains at least metal particles and a digestive enzyme, and that the metal particles have the diameter in the range of 1 nm to 100 nm, and the metal particles are in a dispersed state at normal temperature and pressure. Herein the normal temperature and pressure means 25° C.±5° C. and 101, 325±1,000 Pa.

The treatment solution according to the present invention is used suitably for pretreatment of a sample to be analyzed by TOF-SIMS. Therefore, a metal other than gold may be used, insofar as its particles can enhance the sensitivity of TOF-SIMS. Further, the treatment solution according to the present invention is applied by an ink-jet technique to a predetermined location as droplets. Therefore, the metal particles are required not to plug an outlet of an ink-jet apparatus, and the upper limit of the size of the metal particles is approximately 100 nm. Further, since usually an aqueous solution is used, the metal particles should be in the dispersed state in the aqueous solution. The preferable lower limit of the size of the metal particles is about 1 nm.

The metal particles and the digestive enzyme in the treatment solution according to the present invention are preferably chemically bonded each other (including a coordinate bond), in order to keep the metal particles in a dispersed state for a longer period in the aqueous solution during the application of the treatment solution to a sample by the ink-jet technique. For example, in case gold is used for the metal particles, to bond gold with a digestive enzyme (including a coordinate bond), a thiol group (a mercapto group) and an amino group in the digestive enzyme are generally used.

Further, in the treatment solution according to the present invention, the digestive enzyme is an artificial digestive enzyme. An artificial digestive enzyme means herein an enzyme, which is synthesized artificially, and has at least two sites of a digestive site for digesting and decomposing a protein, and a bonding site with the metal particles. The digestive site for digesting and decomposing a protein is basically same as a digestive active site of pepsin, trypsin, chymotrypsin, etc.

Examples of an object in the sample include a protein in the sample.

In a method for pretreatment according to the present invention, the treatment solution is loaded on an ink-jet apparatus, and the treatment solution is applied by the apparatus to a predetermined location as droplets. As the ink-jet apparatus, apparatuses based on either of a piezo type or a bubble jet type can be used.

A method for acquiring information according to the present invention is a method for acquiring information on an object in a sample, including treating the sample by the abovementioned method for pretreatment, and acquiring by TOF-SIMS information on a mass of the object (including information on masses of peptide fragments decomposed by the digestive enzyme) contained in the treated sample. As a primary ion type for TOF-SIMS is used a monoatomic ion, such as a gallium ion, a cesium ion, a gold ion and a bismuth ion, or a cluster ion, such as an $Au_3$ ion, a $Bi_3$ ion and a $C_{60}$ ion, from viewpoints of ionization efficiency, mass resolution, etc.

In the method for acquiring information according to the present invention, the sample is a slice of a diseased tissue, and the object is a protein.

The present invention further provides a method for detecting the presence of a specific object related to a disease in a sample, and the method for acquiring information is utilized to detect the existence of a specific object related to a disease in the sample.

The present invention can provide a method for identifying with high sensitivity a type of a protein contained in each cell having a diameter of ten to several tens of μm.

Further features of the present invention will become apparent from the following description of exemplary embodiments with reference to the attached drawings.

BRIEF DESCRIPTION OF THE DRAWINGS

FIG. 2 illustrates a DNA sequence with a DNA tag sequence having spacer function for encoding a Cys residue for anchoring to a gold support.

DESCRIPTION OF THE EMBODIMENTS

The present invention is characterized as hereinabove described, and an exemplary embodiment will be described below.

Figure 1:
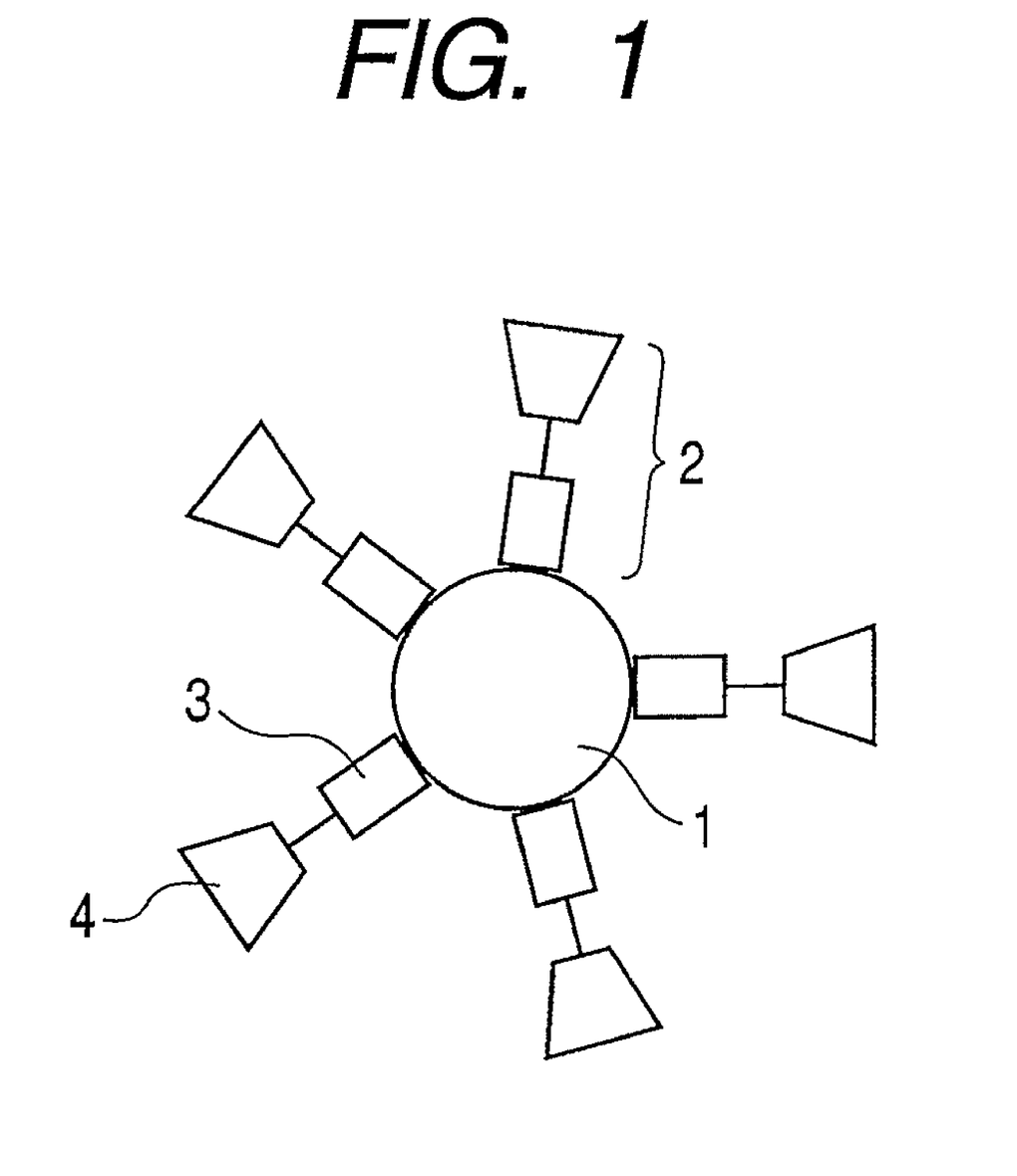
FIG. 1 illustrates a schematic diagram of an artificial digestive enzyme bonded to a gold particle.

A preferable treatment solution according to the present invention is an aqueous solution containing gold particles having a diameter in the range of 1 nm to 100 nm and a digestive enzyme, and they exist in a dispersed state at normal temperature and pressure. It is preferable that the gold particles and the digestive enzyme be chemically bonded together (including a coordinate bond). In the exemplary embodiment, as the digestive enzyme is used an artificial digestive enzyme having a bonding site (with gold particles) having a thiol group (a mercapto group) or an amino group, and a digestive active site of pepsin, trypsin, chymotrypsin, etc. The first reason for the above is higher stability of dispersion in an aqueous solution. The second reason is higher detection sensitivity at the analysis step of TOF-SIMS as further described below. Namely, a gold particle has a function to increase the efficiency of generation of a secondary ion, and consequently a digestion reaction proceeds with higher efficiency in the vicinity of the gold particle, and, as the result, digestion-fragmented peptides can be concentrated in the vicinity of the gold particle. FIG. 1 illustrates a schematic diagram of an artificial digestive enzyme bonded to a gold particle. In FIG. 1 reference numeral 1 denotes a gold particle, reference numeral 2 denotes an artificial digestive enzyme, reference numeral 3 denotes a bonding site with a gold particle in the artificial digestive enzyme 2, and reference numeral 4 denotes a digestive active site in the artificial digestive enzyme 2.

Examples of a sample according to the present invention can include a slice of a diseased tissue, and examples of an object can include a protein in the sample. A further object can include a peptide having a molecular weight less than 10,000.

Basic steps of the method for acquiring information according to the present invention include the following three steps: (1) treating a slice of a diseased tissue with an aqueous solution containing gold particles and a digestive enzyme, and decomposing restrictively a protein of interest, (2) measuring a 2-dimensional distribution of fragmented peptides by TOF-SIMS, and (3) visualizing a 2-dimensional distribution of the protein of interest in the slice of the diseased tissue derived from the result of the proteome analysis and by means of a numerical analysis.

It is preferable to use an ink-jet technique to apply uniformly a digestive enzyme, etc. to a sample in the step (1) above.

Typical measurement conditions of TOF-SIMS in the step (2) are described below.

Kind of the primary ion: a cluster ion, such as an $Au_3$ ion, a $Bi_3$ ion and a $C_{60}$ ion Diameter of the primary ion beam: about 1 µm Fluence (dose) of the primary ion: $1\times10^{14}$ ions/cm$^2$ Measurement area: 100 µm×100 µm Measurement range of mass: 1 to 5,000 (m/z) Measurement time: about 10 min.

A cluster ion is used as the primary ion, because a cluster ion is more advantageous than a monoatomic ion to detect a secondary ion with a large mass number (Japanese Patent No. 3658397). The diameter of the primary ion beam is set at about 1 µm, because it is required to identify an individual cell with a diameter of around 20 µm. For example, each cell can be distinguished by using a raster step-scan of the primary ion over an area of 100 µm×100 µm with 2 µm step which gives 50×50 data points. The fluence of the primary ion is decided as above from the necessity of obtaining secondary ion sensitivity (cumulative signal intensity) beyond a certain level. The measurement range of mass is so selected, because the main object to be measured is digestion-fragmented peptides (e.g. see Japanese Patent Application Laid-Open No. 2006-010658). The measurement time is set to about 10 min, because longer measurement may deteriorate the quantitative evaluation in some cases (e.g. H. Hashimoto, et al., Appl. Surf. Sci., 231-232, 385-391 (2004)).

The numerical analysis in the step (3) above refers to a statistical method, such as factor analysis.

The present invention also relates to a method for detecting the presence of a specific protein related to a disease in a slice of a diseased tissue.

EXAMPLE

The present invention will be described in more detail by way of Examples. The following is an example concerning the exemplary embodiment of the present invention, but it should be noted that the present invention not be limited to such a specific embodiment.

Production and a harvest method of a trypsin recombinant protein is disclosed hereinbelow. In the following Examples, an *E. coli* expression vector for a trypsinogen (a precursor of trypsin) originated from a bovine pancreas is designed, synthesized and expressed in *E. coli* forming an insoluble granular fraction which is subjected to refolding and purification steps, and then a recombinant trypsin protein with enzymatic activity is obtained by autocatalysis. The recombinant DNA method described hereinbelow is based on "Molecular Cloning: A Laboratory Manual" ($2^{nd}$. Edition, by Sambrook, et al., Cold Spring Harbor Laboratory, New York (1989)), and if a commercially available kit is used, those of ordinary skill in the art can perform it following the relevant recommended protocol unless otherwise specified. In order to construct an expression vector, a construct is prepared using a vector pET-Blue-1 belonging to pET-Blue-1 System (Cat. No. 70673-3, Novagen). As a host *E. coli*, for subcloning JM109 strain (Novagen), and for protein production Rosetta (DE3) pLacI strain (Novagen) are used.

Chemical reagents used in Examples are, unless otherwise specified, of high purity grade and commercially available from Sigma-Aldrich, Inc. or Nacalai Tesque, Inc. Commercially available are oligo-DNAs from Sigma Genosys, and restriction enzymes and modification enzymes from Takara Bio Inc.

Example 1

Construction of an Expression Vector for a Gene of Trypsinogen Originated from a Bovine Pancreas Hereinbelow a recombinant gene of trypsinogen originated from a bovine pancreas refers to a DNA sequence (FIG. 2) having a trypsinogen gene coding region (NCBI GenBank accession No. X54703), to which 3'-end is added a DNA tag sequence having spacer function, encoding a His×6 sequence for affinity purification and a Cys residue for anchoring to a gold support.

(1) Synthesis of a Recombinant Gene of Trypsinogen Originated from a Bovine Pancreas Overlap PCR is carried out using Primer set 1 (SEQ ID NOs: 1 to 4), Primer set 2 (SEQ ID NOs: 5 to 10), and Pyrobest DNA polymerase (Takara Bio Inc.) with a mixture ratio recommended by those skilled in the art, and according to a thermal cycle of 98° C. for 1 min–>(98° C. for 10 sec–>55° C. for 30 sec–>72° C. for 30 sec) repeated 40 cycles–>4° C. The resultant amplifications of the fragments with aimed sizes of about 300 bp and 450 bp respectively are confirmed by electrophoresis and EtBr staining.

SEQ ID NO: 1 (5' -> 3')
atgttccctcggacgacgatgacaagatcgtcgggggctacacctgcgc agagaatt SEQ ID NO: 2
ggacaccacccactggtcattgatgagggagccccgcagaagtggtagc cagcattcagggacacctggtaagggacggaattctctgcgcaggtgtag SEQ ID NO: 3
atgaccagtgggtggtgtccgcggctcactgctaccagtaccacatccag gtgaggctgggagaatacaacattgatgtcttggagggtggtgagcagtt SEQ ID NO: 4
agagtttgatcagcaggatgtcattgtccagagtccagctgctgtacttg gggtggcggatgatcttggacgcatcgatgaactgctcaccaccctccaa SEQ ID NO: 5
catcctgctgatcaaactctccacgcctgcggtcatcaatgcccgggtgt ccaccttgctgctgcccagtgcctgtgcttccgcaggcacagagtgcctc SEQ ID NO: 6
ctcagcagcgggccaccaggcattgcagcaggtccgggtagttgacgcc actgctcagggtgttgccccagccggagatgaggcactctgtgcctgcgg SEQ ID NO: 7
ctggtggccccgctgctgagccacgccgactgtgaagcctcatccctgg acagatcactaacaacatgatctgcgctggcttcctggaaggaggcaagg -continued SEQ ID NO: 8
acagccgtagcccaggacacaatgccctggagctgtccgttgcaagcca cagggccgccagagtcaccctggcaggaatccttgcctccttccaggaag SEQ ID NO: 9
tgtcctggggctacggctgtgcccagaagggcaagcctggggtctacacc aaggtctgcaactacgtggactggattcaggagaccatcgccgccaacag SEQ ID NO: 10
ggcttagcaatggtggtgatgatggtggctagcgctgttggcggcgatgg tctc Next, the fragments of the aimed sizes are purified by a commercially available gel purification kit (Wizard SV Gel and PCR Clean-Up system (Cat. No. # A9281, Promega Corp.)). Then using the two fragments as templates and Primer set 3 (SEQ ID NOs: 11 and 12), overlap PCR is carried out according to the same conditions. After confirming that the fragment with final aimed size of about 730 bp is amplified, the same is purified similarly.

atgttccctcggacgacgatga      SEQ ID NO: 11 ggcttagcaatggtggtgatgat      SEQ ID NO: 12

(2) Subcloning to an *E. Coli* Expression Vector

The pET-Blue-1 expression vector is digested by an EcoRV enzyme, and is subjected to dephosphorylation with BAP (37° C., 1 hour). The dephosphorylated DNA fragments are purified with the Wizard SV Gel and PCR Clean-Up system (Cat. No. # A9281, Promega Corp.). Then the dephosphorylated vector is ligated with the DNA fragment synthesized in (1) above using a commercially available DNA ligation kit (Ligation High Code No. LGK-101 (Toyobo Co.)) by a method recommended by the producer.

With the ligation solution a competent cell of JM109 strain (Novagen) is transformed by a heat-shock method, and plated on an agar plate with Luria-Bertani medium (LB)+Amp. (100 μg/mL)+IPTG+X-gal, and the plate is left stand overnight at 37° C.

After blue-white selection a colony of choice is inoculated into 3 mL of an LB/Amp liquid medium and shaking-cultured at 37° C. overnight. Then a plasmid DNA is harvested using a commercially available MiniPrep kit (Plus Minipreps DNA Purification System (Promega Corp.)).

The base sequence of the harvested plasmid is determined. If it can be confirmed that the subject fragment is inserted in a correct direction and the sequence is correct, an expression vector for a recombinant trypsinogen gene originated from a bovine pancreas is complete.

Example 2

Experiment of Expressing Trypsinogen Recombinant Protein in *E. Coli* and Refolding (1) Transformation The expression vector obtained in Example 1 is added for transformation to a solution of Rosetta (DE3) pLacI strain competent cells for protein production. Transformation is carried out by a heat shock under the conditions of: on ice–>42° C. for 90 sec–>on ice. Into the solution of the Rosetta (DE3) pLacI strain competent cells transformed by the heat shock, 500 μL of Terrific broth medium (TB, 1% (W/V) yeast extract, 2% (W/V) peptone, 0.1M phosphate buffer (pH 7.5), 1% glycerol) is added, followed by a shaking culture for 1 hour at 37° C. The mixture is then centrifuged at 5,000 rpm for 5 min, and 650 μL of the culture supernatant is discarded. The remaining culture supernatant and the precipitated cell fraction are mixed together and plated on an agar plate with TB/Amp. 100 μg/mL/chloramphenicol 34 μg/mL, which is incubated overnight at 37° C.

(2) Preculture

A colony on the plate is selected randomly and shaking-cultured in 50 mL of a TB/Amp. 200 μg/mL/chloramphenicol 34 μg/mL medium at 37° C. until the OD value at 600 nm falls within 0.2 to 0.6. Then the solution is centrifuged at 1,000×g for 5 min, and, discarding the supernatant, the bacterial cells are collected and suspended in a fresh identical medium. Two mL of the suspension is inoculated into 500 mL of a TB/Amp. 400 μg/mL/chloramphenicol 34 μg/mL medium and shaking-cultured at 37° C. until the OD value at 600 nm falls within 0.2 to 0.6.

(3) Main Culture

The preculture solution is cultured further at 30° C. When the OD value at 600 nm exceeds 1.0, IPTG is added to a final concentration of 1 mM, and the culture is continued at 30° C. overnight.

(4) Purification

The aimed polypeptide chain is purified out of an insoluble granular fraction according to the following steps.

(i) Recovery of an Insoluble Granular Fraction

The culture solution obtained in (3) above is centrifuged at 6,000 rpm for 30 min to obtain a bacterial cell fraction as the precipitate. The recovered bacterial cells are suspended in 15 mL of a Tris solution (20 mM Tris-HCl (pH 8.0)/500 mM NaCl) containing 100 μg/mL of lysozyme, and, after incubated at 37° C. for 30 min, stored on ice. The obtained suspension is disrupted by a French press to obtain a disrupted bacterial cell solution. After adding 10 unit of a DNase I enzyme, the solution is incubated at 37° C. for 15 min. Then, with addition of Triton X-100 to the final concentration of 2%, an insoluble granular fraction is washed twice.

Then the disrupted bacterial cell solution was centrifuged at 12,000 rpm for 15 min, and after removal of the supernatant, the precipitate is recovered as the insoluble granular fraction.

(ii) Solubilization of the Insoluble Granular Fraction

Ten mL of a 6 M guanidine hydrochloride/Tris solution (20 mM Tris-HCl (pH 8.0)/500 mM NaCl) is added to the insoluble granular fraction obtained in (i) above, which is then dispersed by ultrasonication, and left dipped in the liquid overnight at room temperature. The liquid is centrifuged at 12,000 rpm for 10 min, and the supernatant is recovered as a solubilized solution.

(iii) A Metal Chelate Column

As a support of a metal chelate column is used His-Bind (Novagen). Column conditioning, sample loading and washing steps are based on the recommended method by the producer, and carried out at room temperature (20° C.). The aimed His-tag fused polypeptide is eluted by a 60 mM imidazole/Tris solution. The eluate is examined by SDS-PAGE (acrylamide 15%) to find if a single band confirming adequate purification is obtained.

(iv) Dialysis

The eluate is dialyzed using a 6 M guanidine hydrochloride/Tris solution as an external solution at 4° C. for removal of imidazole in the eluate to obtain the polypeptide chain solution.

(v) Refolding

Similarly as in above the polypeptide chain solution is subjected to dialysis at 4° C. for removal of guanidine hydrochloride, during which refolding of a protein is carried out.

(a) With a 6 M guanidine hydrochloride/Tris solution, a sample of the concentration of 7.5 μM (volume after dilution 10 mL) is prepared using the molar absorption coefficient of the polypeptide chain and the ΔO.D. value (280 nm to 320 nm). Then β-mercaptoethanol (a reducing agent) is added to the final concentration of 375 μM (50-fold of the protein concentration) and the sample is reduced at room temperature in dark for 4 hours. The sample solution is packed in a dialysis bag (MWCO: 8,000) to prepare a dialysis sample.

(b) The dialysis sample is dipped into an external dialysis solution of a 6 M guanidine hydrochloride/Tris solution, and dialyzed under gentle agitation for 6 hours.

(c) The concentration of the external guanidine hydrochloride/Tris solution is lowered stepwise to 3M and 2M, dialyzing for 6 hours at each concentration of the external solution.

(d) Into a Tris solution are added oxidized glutathione (GSSG) to the final concentration of 375 μM, and L-Arg to the final concentration of 0.4 M. Into this solution the 2 M external dialysis solution of (c) above is added to the concentration of guanidine hydrochloride of 1 M, and the pH of the solution is adjusted to 8.0 (4° C.) with NaOH. The sample is dialyzed with the solution for 12 hours under gentle agitation.

(e) According to a similar procedure as (d) above, a Tris solution with 0.5 M guanidine hydrochloride concentration, containing L-Arg is prepared, and used for dialysis for 12 hours.

(f) Finally, the sample is dialyzed with a Tris solution for 12 hours.

(g) After the completion of the dialysis, the sample is centrifuged at 10,000 rpm for about 20 min to separate an aggregate and a supernatant to obtain a soluble refolded trypsinogen recombinant protein.

Example 3

Activation of a Trypsinogen Recombinant Protein and Purification and Recovery of the Active Trypsin Recombinant Protein (1) Activation of a Trypsinogen Recombinant Protein The obtained soluble refolded trypsinogen recombinant protein is left at room temperature for 1 hour, and then left standing at 4° C. for 12 hours to obtain a trypsin recombinant protein autocatalytically.

(2) Purification by Chromatography

Five μM of the soluble refolded trypsin recombinant protein solution obtained in (1) above is subjected to gel filtration using a Superdex 200 column (GE Healthcare) (Buffer: 20 mM Tris-HCl (pH 8.0), 500 mM of NaCl, flow velocity: 0.5 mL/min) to obtain a single peak fraction of the aimed size.

(3) Measurement of Trypsin Activity

The method by Erlanger et al. using N-benzoyl-DL-arginine-p-nitroanilide hydrochloride (BAPA) as a substrate (a BAPA method) is applied. A sub-fraction of the above-described fractions is reacted with the substrate at 25° C. for 5 min, and then the optical density at 405 nm of p-nitroaniline, a decomposition product of BAPA, is measured. The fraction with the highest activity is harvested. As the result, an active trypsin recombinant protein is obtained. The protein is used for the following tests.

Example 4

Preparation of an Aqueous Solution Containing the Trypsin Recombinant Protein and Gold Particles, and Application of the Aqueous Solution to a Sample Using an Ink-Jet Printer From the starting material of a solution containing gold particles with an average diameter of about 40 nm (dispersant: citric acid), using a conventional method, an aqueous solution is prepared as the treatment solution according to the present invention, in which the trypsin recombinant protein and the gold particles are bonded together. Whether the aqueous solution is in well dispersed condition or not, can be determined, for instance, by leaving it stand at room temperature for about 2 days and observing if precipitation takes place or not. The aqueous solution is loaded on a bubble-jet printer described in the specification of Japanese Patent No. 3658397 to the present inventors. More particularly, a printer-head BC-50 (Canon Inc.) for a bubble-jet printer BJF-850 (Canon Inc.) is so modified and used that it can extrude some hundreds μL of a solution, and some hundreds μL of the aqueous solution is filled in a head tank. Samples placed on a silicon substrate are inserted to the printer, and droplets of the aqueous solution are applied all over the sample surfaces. Thereby care should be taken with respect to uniformity of the final quantity of the applied solution, which should be 2-dimensionally uniform in order to digest the protein in the surface layer uniformly, (for example, by shifting gradually the application spot of droplets). The droplet volume is usually 1 to 8 pL/droplet and a number of applications at a certain spot (number of layers) is adjusted in accordance with the concentration of the trypsin recombinant protein. The concentration of the trypsin recombinant protein is selected between about 1 and 100 μM. After the application of the aqueous solution to the sample, it is necessary to keep it at normal temperature and under high humidity for a predetermined time for the progress of the digestion reaction.

The aqueous solution to be used by the bubble-jet printer may contain one or more selected from the group consisting of glycerin, urea, thiodiglycol and acetylenic alcohol (acetylenol EH® Kawaken Fine Chemicals Co.) for the purpose of stabilizing the extrusion, and the like.

Example 5

TOF-SIMS Analysis of Trypsin Digestion Products of Human Serum Albumin (HSA)

Human serum albumin (HSA, amino acid SEQ ID NO: 13) is spin-coated on a silicon substrate etc., and digested and decomposed by the method in Example 4.

```
                                              SEQ ID NO: 13
mkwvtfisllflfssaysrgvfrrdahksevahrfkdlgeenfkalvlia faqylqqcpfedhvklvnevtefaktcvadesaencdkslhtlfgdklct atlretygemadccakqepernecflqhkddnpnlprlvrpevdvmctaf hdneetflkkylyeiarrhpyfyapellfffakrykaafteccqaadkaac llpkldelrdegkassakqrlkcaslqkfgerafkawavarlsqrfpkae faevsklvtdltkvhtecchgdllecaddadlayicenqdsissklkecc ekpllekshciaevendempadlpslaadfveskdvcknyaeakdvflgm flyeyarrhpdysvvlllrlaktyettlekccaaadphecyakvfdefkp lveepqnlikqncelfeqlgeykfqnallvrytkkvpqvstptlvevsrn
```

-continued lgkvgskcckhpeakrmpcaedylsvvlnqlcvlhektpvsdrvtkccte slvnrrpcfsalevdetyvpkefnaetftfhadictlsekerqikkqtal velvkhkpkatkeqlkavmddfaafvekcckaddketcfaeegkklvaas qaalgl By the digestion/decomposition treatment, the chain is selectively cut basically at the right hand side of k and r in the above sequence of SEQ ID NO: 13, to generate many peptide fragments. Among the peptide fragments, a characteristic peptide, such as dahk, sevahr, necflqhk, hpyfyapellffak, caslqk, aefaevsk, lvtdltk, adlayicenqdsissk, dvflgmflyeyar, hpdysvvlllr, vpqvstptlvevsrvgsk, cckhpeak, tpvsdr, ccteslvnr, erqik, avmddfaafvek, lvaasqaalgl is detected in the form of a protonated molecule or an adduct ion with gold by TOF-SIMS. The molecular weights of them are in the range of about 500 to 5000 m/z. A plurality of characteristic fragments of peptide as indicated above, can be detected to determine whether the protein before the digestion/decomposition is HSA. In this case, by coexistence of gold particles in the sample surface layer, the detection sensitivity of a secondary ion is increased and the identification accuracy is improved.

Example 6

Figure 3:
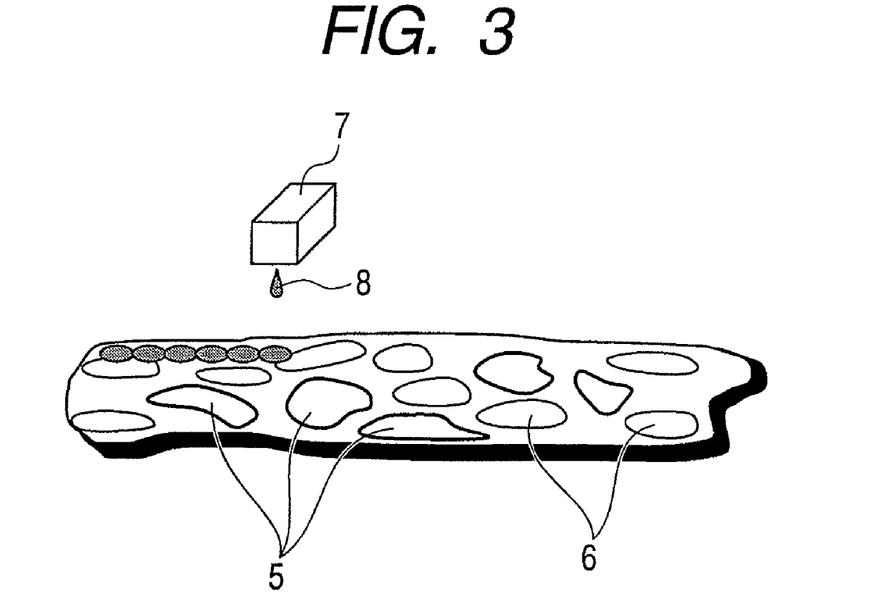
FIG. 3 illustrates a schematic diagram of a step of applying the aqueous solution containing gold particles and a digestive enzyme to a slice of human cancer tissue by an ink-jet technique.

TOF-SIMS Analysis of Trypsin Digestion Products of a Slice of Human Cancer Tissue A slice of 0.5 to 5 μm thickness and 1 to 10 mm² size is cut from a human cancer tissue, placed on a substrate, and digested according to the method described in Example 4. FIG. 3 illustrates a schematic diagram thereof. In FIG. 3 reference numeral 5 denotes an abnormal cell in the cancer tissue slice, reference numeral 6 denotes a normal cell in the cancer tissue slice, reference numeral 7 denotes an ink-jet printer head, and reference numeral 8 denotes a droplet.

Figure 4:
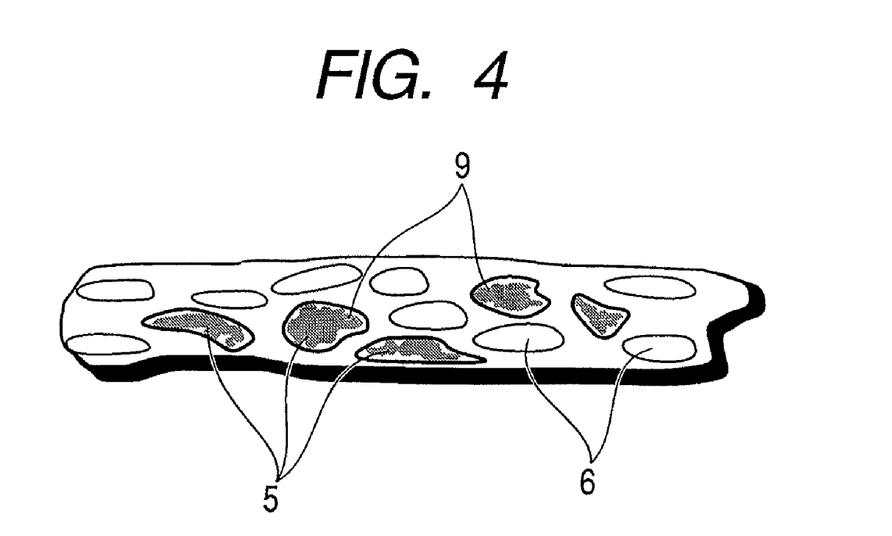
FIG. 4 illustrates an example of a 2-dimensional display of locations of a protein of interest (locations of a protein related to recurrence or metastasis) identified by detection patterns of peptide fragments.

After the digestion/decomposition treatment, the digested and decomposed peptides are detected by TOF-SIMS as in Example 5. Thereafter, for example, a protein related to recurrence or metastasis is identified by fragmented peptide patterns, and rebuilt to display a 2-dimensional distribution of their signal intensities. A schematic diagram is depicted in FIG. 4. In FIG. 4 reference numeral 9 denotes a location of a protein of interest (a location of the protein related to recurrence or metastasis). As described above, the method of the present invention can be used to know a location of a protein of interest on a cell level. In this case, by coexistence of gold particles in the sample surface layer, the detection sensitivity of a secondary ion is increased, and, as the result, the identification accuracy of the protein of interest is improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-118899, filed Apr. 27, 2007, which is hereby incorporated by reference herein in its entirety.

What is claimed is:

1. A method of acquiring information of an object in a sample, wherein the object is decomposed by an artificial digestive enzyme, comprising the steps of:
treating the sample with a treatment solution by applying the treatment solution to the sample by an ink-jet method, wherein the treatment solution comprises at least a gold particle and the artificial digestive enzyme, the artificial digestive enzyme has a digestive active site and a bonding site with the gold particle, the gold particle and the artificial digestive enzyme are chemically bonded, the gold particle exists in a dispersed state at normal temperature and pressure, and the treatment solution further contains one or more selected from the group consisting of glycerin, urea, thiodiglycol and acetylenic alcohol; and
acquiring information on a mass of the object by time of flight secondary ion mass spectrometry, wherein the information on the mass of the object includes information on masses of peptide fragments decomposed by the artificial digestive enzyme.

2. The method according to claim 1, wherein the bonding site comprises a thiol group or an amino group.

3. A method of acquiring information of an object in a sample, wherein the object is decomposed by an artificial digestive enzyme, comprising the steps of:
treating the sample with a treatment solution, wherein the treatment solution comprises a gold particle in a dispersed state at normal temperature and pressure and the artificial digestive enzyme, the artificial digestive enzyme has a digestive active site and a bonding site with the gold particle, the gold particle and the artificial digestive enzyme are chemically bonded, the diameter of the gold particle is in the range of 1 nm to 100 nm, the treatment solution further contains one or more selected from the group consisting of glycerin, urea, thiodiglycol and acetylenic alcohol, and the treatment solution is loaded on an ink-jet apparatus and applied as droplets by the apparatus to a predetermined location of the sample; and
acquiring information on a mass of the object contained in the treated sample, wherein the information on the mass of the object includes information on masses of peptide fragments decomposed by the artificial digestive enzyme.

* * * * *

SEQUENCE LISTING

<160> NUMBER OF SEQ ID NOS: 15

<210> SEQ ID NO 1
<211> LENGTH: 58
<212> TYPE: DNA
<213> ORGANISM: Artificial
<220> FEATURE:
<223> OTHER INFORMATION: Primer

<400> SEQUENCE: 1
atgttcccct cggacgacga tgacaagatc gtcgggggct acacctgcgc agagaatt      58

<210> SEQ ID NO 2
<211> LENGTH: 100
<212> TYPE: DNA
<213> ORGANISM: Artificial
<220> FEATURE:
<223> OTHER INFORMATION: Primer

<400> SEQUENCE: 2
ggacaccacc cactggtcat tgatgaggga gcccccgcag aagtggtagc cagcattcag      60
ggacacctgg taagggacgg aattctctgc gcaggtgtag                          100

<210> SEQ ID NO 3
<211> LENGTH: 100
<212> TYPE: DNA
<213> ORGANISM: Artificial
<220> FEATURE:
<223> OTHER INFORMATION: Priemr

<400> SEQUENCE: 3
atgaccagtg ggtggtgtcc gcggctcact gctaccagta ccacatccag gtgaggctgg      60
gagaatacaa cattgatgtc ttggagggtg gtgagcagtt         100

<210> SEQ ID NO 4
<211> LENGTH: 100
<212> TYPE: DNA
<213> ORGANISM: Artificial
<220> FEATURE:
<223> OTHER INFORMATION: Primer

<400> SEQUENCE: 4
agagtttgat cagcaggatg tcattgtcca gagtccagct gctgtacttg gggtggcgga         60
tgatcttgga cgcatcgatg aactgctcac caccctccaa         100

<210> SEQ ID NO 5
<211> LENGTH: 100
<212> TYPE: DNA
<213> ORGANISM: Artificial
<220> FEATURE:
<223> OTHER INFORMATION: Primer

<400> SEQUENCE: 5
catcctgctg atcaaactct ccacgcctgc ggtcatcaat gcccgggtgt ccaccttgct         60
gctgcccagt gcctgtgctt ccgcaggcac agagtgcctc         100

<210> SEQ ID NO 6
<211> LENGTH: 100
<212> TYPE: DNA
<213> ORGANISM: Artificial
<220> FEATURE:
<223> OTHER INFORMATION: Primer

<400> SEQUENCE: 6
ctcagcagcg gggccaccag gcattgcagc aggtccgggt agttgacgcc actgctcagg         60
gtgttgcccc agccggagat gaggcactct gtgcctgcgg         100

<210> SEQ ID NO 7
<211> LENGTH: 100
<212> TYPE: DNA
<213> ORGANISM: Artificial
<220> FEATURE:
<223> OTHER INFORMATION: Primer

<400> SEQUENCE: 7
ctggtggccc cgctgctgag ccacgccgac tgtgaagcct catccctgg acagatcact         60 aacaacatga tctgcgctgg cttcctggaa ggaggcaagg         100

<210> SEQ ID NO 8
<211> LENGTH: 100
<212> TYPE: DNA
<213> ORGANISM: Artificial
<220> FEATURE:
<223> OTHER INFORMATION: Primer

<400> SEQUENCE: 8
acagccgtag ccccaggaca caatgccctg gagctgtccg ttgcaagcca cagggccgcc         60
agagtcaccc tggcaggaat ccttgcctcc ttccaggaag         100

<210> SEQ ID NO 9
<211> LENGTH: 100
<212> TYPE: DNA
<213> ORGANISM: Artificial
<220> FEATURE:
<223> OTHER INFORMATION: Primer

<400> SEQUENCE: 9

```
tgtcctgggg ctacggctgt gcccagaagg gcaagcctgg ggtctacacc aaggtctgca    60
actacgtgga ctggattcag gagaccatcg ccgccaacag                         100
```

<210> SEQ ID NO 10
<211> LENGTH: 54
<212> TYPE: DNA
<213> ORGANISM: Artificial
<220> FEATURE:
<223> OTHER INFORMATION: Primer

<400> SEQUENCE: 10

```
ggcttagcaa tggtggtgat gatggtggct agcgctgttg gcggcgatgg tctc          54
```

<210> SEQ ID NO 11
<211> LENGTH: 23
<212> TYPE: DNA
<213> ORGANISM: Artificial
<220> FEATURE:
<223> OTHER INFORMATION: Primer

<400> SEQUENCE: 11

```
atgttcccct cggacgacga tga                                            23
```

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12

```
ggcttagcaa tggtggtgat gat                                            23
```

<210> SEQ ID NO 13
<211> LENGTH: 606
<212> TYPE: PRT
<213> ORGANISM: Homo sapiens

<400> SEQUENCE: 13

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Ala Thr Leu Arg Glu Thr Tyr Gly Glu Met Ala Asp
            100                 105                 110

Cys Cys Ala Lys Gln Glu Pro Glu Arg Asn Glu Cys Phe Leu Gln His
        115                 120                 125

Lys Asp Asp Asn Pro Asn Leu Pro Arg Leu Val Arg Pro Glu Val Asp
    130                 135                 140

Val Met Cys Thr Ala Phe His Asp Asn Glu Glu Thr Phe Leu Lys Lys
145                 150                 155                 160
```

```
Tyr Leu Tyr Glu Ile Ala Arg Arg His Pro Tyr Phe Tyr Ala Pro Glu
                165                 170                 175

Leu Leu Phe Phe Ala Lys Arg Tyr Lys Ala Phe Thr Glu Cys Cys
        180                 185                 190

Gln Ala Ala Asp Lys Ala Ala Cys Leu Leu Pro Lys Leu Asp Glu Leu
            195                 200                 205

Arg Asp Glu Gly Lys Ala Ser Ser Ala Lys Gln Arg Leu Lys Cys Ala
210                 215                 220

Ser Leu Gln Lys Phe Gly Glu Arg Ala Phe Lys Ala Trp Ala Val Ala
225                 230                 235                 240

Arg Leu Ser Gln Arg Phe Pro Lys Ala Glu Phe Ala Glu Val Ser Lys
                245                 250                 255

Leu Val Thr Asp Leu Thr Lys Val His Thr Glu Cys Cys His Gly Asp
            260                 265                 270

Leu Leu Glu Cys Ala Asp Asp Ala Asp Leu Ala Tyr Ile Cys Glu Asn
            275                 280                 285

Gln Asp Ser Ile Ser Ser Lys Leu Lys Glu Cys Cys Glu Lys Pro Leu
290                 295                 300

Leu Glu Lys Ser His Cys Ile Ala Glu Val Glu Asn Asp Glu Met Pro
305                 310                 315                 320

Ala Asp Leu Pro Ser Leu Ala Ala Asp Phe Val Glu Ser Lys Asp Val
                325                 330                 335

Cys Lys Asn Tyr Ala Glu Ala Lys Asp Val Phe Leu Gly Met Phe Leu
            340                 345                 350

Tyr Glu Tyr Ala Arg Arg His Pro Asp Tyr Ser Val Val Leu Leu Leu
            355                 360                 365

Arg Leu Ala Lys Thr Tyr Glu Thr Thr Leu Glu Lys Cys Cys Ala Ala
370                 375                 380

Ala Asp Pro His Glu Cys Tyr Ala Lys Val Phe Asp Glu Phe Lys Pro
385                 390                 395                 400

Leu Val Glu Glu Pro Gln Asn Leu Ile Lys Gln Asn Cys Glu Leu Phe
                405                 410                 415

Glu Gln Leu Gly Glu Tyr Lys Phe Gln Asn Ala Leu Leu Val Arg Tyr
            420                 425                 430

Thr Lys Lys Val Pro Gln Val Ser Thr Pro Thr Leu Val Glu Val Ser
            435                 440                 445

Arg Asn Leu Gly Lys Val Gly Ser Lys Cys Cys Lys His Pro Glu Ala
450                 455                 460

Lys Arg Met Pro Cys Ala Glu Asp Tyr Leu Ser Val Val Leu Asn Gln
465                 470                 475                 480

Leu Cys Val Leu His Glu Lys Thr Pro Val Ser Asp Arg Val Thr Lys
                485                 490                 495

Cys Cys Thr Glu Ser Leu Val Asn Arg Arg Pro Cys Phe Ser Ala Leu
            500                 505                 510

Glu Val Asp Glu Thr Tyr Val Pro Lys Glu Phe Asn Ala Glu Thr Phe
            515                 520                 525

Thr Phe His Ala Asp Ile Cys Thr Leu Ser Glu Lys Glu Arg Gln Ile
530                 535                 540

Lys Lys Gln Thr Ala Leu Val Glu Leu Val Lys His Lys Pro Lys Ala
545                 550                 555                 560

Thr Lys Glu Gln Leu Lys Ala Val Met Asp Asp Phe Ala Ala Phe Val
                565                 570                 575

Glu Lys Cys Cys Lys Ala Asp Asp Lys Glu Thr Cys Phe Ala Glu Glu
```

-continued

```
            580                 585                 590
Gly Lys Lys Leu Val Ala Ala Ser Gln Ala Ala Leu Gly Leu
        595                 600                 605
```

<210> SEQ ID NO 14
<211> LENGTH: 768
<212> TYPE: DNA
<213> ORGANISM: Artificial
<220> FEATURE:
<223> OTHER INFORMATION: DNA coding recombinant protein

<400> SEQUENCE: 14

```
atgcatcccc tgcttatcct tgcctttgtg ggagctgctg tggctttccc ctcggacgac    60
gatgacaaga tcgtcggggg ctacacctgc gcagagaatt ccgtccctta ccaggtgtcc   120
ctgaatgctg gctaccactt ctgcgggggc tccctcatca atgaccagtg gtggtgtcc    180
gcggctcact gctaccagta ccacatccag gtgaggctgg agaatacaa cattgatgtc    240
ttggagggtg gtgagcagtt catcgatgcg tccaagatca tccgccaccc caagtacagc   300
agctggactc tggacaatga catcctgctg atcaaactct ccacgcctgc ggtcatcaat   360
gcccgggtgt ccaccttgct gctgcccagt gcctgtgctt ccgcaggcac agagtgcctc   420
atctccggct ggggcaacac cctgagcagt ggcgtcaact acccggacct gctgcaatgc   480
ctggtggccc gctgctgag ccacgccgac tgtgaagcct cataccctgg acagatcact   540
aacaacatga tctgcgctgg cttcctggaa ggaggcaagg attcctgcca gggtgactct   600
ggcggccctg tggcttgcaa cggacagctc cagggcattg tgtcctgggg ctacggctgt   660
gcccagaagg gcaagcctgg ggtctacacc aaggtctgca actacgtgga ctggattcag   720
gagaccatcg ccgccaacag cgctagccac catcatcacc accattgc                768
```

<210> SEQ ID NO 15
<211> LENGTH: 256
<212> TYPE: PRT
<213> ORGANISM: Artificial
<220> FEATURE:
<223> OTHER INFORMATION: Recombinant protein

<400> SEQUENCE: 15

```
Met His Pro Leu Leu Ile Leu Ala Phe Val Gly Ala Ala Val Ala Phe
1               5                   10                  15

Pro Ser Asp Asp Asp Lys Ile Val Gly Gly Tyr Thr Cys Ala Glu
            20                  25                  30

Asn Ser Val Pro Tyr Gln Val Ser Leu Asn Ala Gly Tyr His Phe Cys
        35                  40                  45

Gly Gly Ser Leu Ile Asn Asp Gln Trp Val Val Ser Ala Ala His Cys
    50                  55                  60

Tyr Gln Tyr His Ile Gln Val Arg Leu Gly Glu Tyr Asn Ile Asp Val
65                  70                  75                  80

Leu Glu Gly Gly Glu Gln Phe Ile Asp Ala Ser Lys Ile Ile Arg His
                85                  90                  95

Pro Lys Tyr Ser Ser Trp Thr Leu Asp Asn Asp Ile Leu Leu Ile Lys
            100                 105                 110

Leu Ser Thr Pro Ala Val Ile Asn Ala Arg Val Ser Thr Leu Leu Leu
        115                 120                 125

Pro Ser Ala Cys Ala Ser Ala Gly Thr Glu Cys Leu Ile Ser Gly Trp
    130                 135                 140

Gly Asn Thr Leu Ser Ser Gly Val Asn Tyr Pro Asp Leu Leu Gln Cys
145                 150                 155                 160
```

```
Leu Val Ala Pro Leu Leu Ser His Ala Asp Cys Glu Ala Ser Tyr Pro
            165             170             175

Gly Gln Ile Thr Asn Asn Met Ile Cys Ala Gly Phe Leu Glu Gly Gly
            180             185             190

Lys Asp Ser Cys Gln Gly Asp Ser Gly Gly Pro Val Ala Cys Asn Gly
        195             200             205

Gln Leu Gln Gly Ile Val Ser Trp Gly Tyr Gly Cys Ala Gln Lys Gly
    210             215             220

Lys Pro Gly Val Tyr Thr Lys Val Cys Asn Tyr Val Asp Trp Ile Gln
225             230             235             240

Glu Thr Ile Ala Ala Asn Ser Ala Ser His His His His His His Cys
            245             250             255
```